United States Patent
Ham

(10) Patent No.: US 9,457,015 B2
(45) Date of Patent: Oct. 4, 2016

(54) 2-AMINOTHIAZOLE DERIVATIVE AND ANTI-CANCER COMPOSITION COMPRISING SAME AS ACTIVE INGREDIENT

(71) Applicant: Chung-Ang University Industry-Academic Cooperation Foundation, Seoul (KR)

(72) Inventor: Seung Wook Ham, Seoul (KR)

(73) Assignee: Chung-Ang University Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 14/369,904

(22) PCT Filed: Oct. 30, 2012

(86) PCT No.: PCT/KR2012/008989
§ 371 (c)(1),
(2) Date: Jun. 30, 2014

(87) PCT Pub. No.: WO2013/122303
PCT Pub. Date: Aug. 22, 2013

(65) Prior Publication Data
US 2015/0368235 A1 Dec. 24, 2015

(30) Foreign Application Priority Data
Feb. 17, 2012 (KR) ........................ 10-2012-0016246

(51) Int. Cl.
*A61K 31/427* (2006.01)
*C07D 417/12* (2006.01)

(52) U.S. Cl.
CPC ........... *A61K 31/427* (2013.01); *C07D 417/12* (2013.01)

(58) Field of Classification Search
CPC ........................... C07D 417/12; A61K 31/427
See application file for complete search history.

(56) References Cited

U.S. PATENT DOCUMENTS

2006/0052416 A1  3/2006  Dickson
2006/0063814 A1  3/2006  Goodnow

FOREIGN PATENT DOCUMENTS

WO    WO 2011/076732    6/2011

OTHER PUBLICATIONS

Wang et al. Expert Opin. Ther. Patents 2009, 19, 305-319.*
Luo et al. Cell 2009, 136, 823-837.*
Gura, Science Nov. 7, 1997: vol. 278. No. 5340, pp. 1041-1042.*
Leaf, Clifton, Health Administrator vol. XVII, No. 1: 172-183, 2005.*
"Expert Scientific Group on Phase One Clinical Trials Final Report" Nov. 30, 2006, pp. Cl, C35-C38.*
Cancer Drug Design and Discovery Neidle, Stephen, ed. (Elsevier/Academic Press, 2008) p. 427.*
Kamb, Nature Reviews Drug Discovery 4, 161-165 (Feb. 2005).*
Isanbor et al. Journal of Fluorine Chemistry 2006, 127, 303-319.*
Li et al. Bull. Korean Chem. Soc. 2010, 31, 1463-1464.*
Kim et al. Bull. Korean Chem. Soc. 2011, 32, 2893-2894.*
Jinyeong Kim et al, "2-Aminothiazole Derivative as a New Class of TrkA Kinase Inhibitor", *Bull. Korean Chem. Soc.*, 2011, vol. 32, No. 8, pp. 2893-2894.
Minghua Li et al, "A Novel Aminothiazole Derivative Induces Apoptosis and Cell Cycle Arrest in Tumor Cells", *Bull. Korean Chem. Soc.*, 2010, vol. 31, No. 11, pp. 3454-3456.
Borzilleri RM, et al., "Discovery and Evaluation of N-Cyclopropyl-2,4-difluoro-5-((2-(pyridin-2-ylamino)thiazol-5-ylmethyl)amino)benzamide (BMS-605541), a Selective and Orally Efficacious Inhibitor of Vascular Endothelial Growth Factor Receptor-2," *J Med Chem*, 49:1 3766-3769, 2006.
Foley PL et al., "Considerations for the Design and Construction of aSynthetic Platform Cell for Biotechnological Applications," *Biotechnol Bioeng*, 105: 26-36, 2010.
Helal et al., "Discovery and SAR of 2-aminothiazole inhibitors ofcyclin-dependent kinase 5/p25 as a potential treatment for Alzheimer's disease," *Bioorg Med Chem Lett*, 14: 5521-5525, 2004.
Hook AL, et al., "High throughput methods applied in biomaterial development and discovery" *Biomaterials*, 2: 187-198, 2010.
Jung FH et al., "Discovery of Novel and Potent Thiazoloquinazolines as Selective Aurora A and B Kinase Inhibitors," *J Med Chem*, 49: 955-970, 2006.
Kim KS et al., "Discovery of Aminothiazole Inhibitors of Cyclin-Dependent Kinase 2: Synthesis, X-ray Crystallographic Analysis, and Biological Activities," *J Med Chem*, 45: 3905-3927, 2002.
Kuramoto M, et al., "Preparation of leukotriene B4 inhibitory active 2- and 3-(2-aminothiazol-4-yl)benzo[b]furan derivatives and their growth inhibitory activity on human pancreatic cancer cells†," *Org Biomol Chem*, 6: 2772-2781, 2008.

(Continued)

*Primary Examiner* — Matthew Coughlin
(74) *Attorney, Agent, or Firm* — Riverside Law LLP

(57) ABSTRACT

The present invention relates to a novel 2-aminothiazole derivative, N-(5-(4-fluorophenyl)thiazole-2-il)-3-(furan-2-il)propane amide and to a use thereof as an anti-cancer drug. It is verified that the compound of the present invention has highly superior cancer cell-specific cytotoxic activity and in-vivo anti-cancer activity for inhibiting the growth of tumors in an animal model for cancer disease, and therefore can be developed as an anti-cancer candidate substance.

1 Claim, 3 Drawing Sheets

(56) References Cited

OTHER PUBLICATIONS

Misra RN, et al., "N-(Cycloalkylamino)acyl-2-aminothiazole Inhibitors of Cyclin-Dependent Kinase 2. N-[5-[[[5-(1,1-Dimethylethyl)-2-oxazolyl]methyl]thio]-2-thiazolyl]-4-piperidinecarboxamide (BMS-387032), a Highly Efficacious and Selective Antitumor Agent," *J Med Chem*, 47: 1719-1728, 2004.

Romagnoli R, et al., "2-Arylamino-4-Amino-5-Aroylthiazoles. "One-Pot" Synthesis and Biological Evaluation of a New Class of Inhibitors of Tubulin Polymerization," *J Med Chem*, 52: 5551-5555, 2009.

\* cited by examiner

Vehicle (DMSO:PEG400:DW=5:40:55) 100μL

HF154 2mpk 100μL

2-AMINOTHIAZOLE DERIVATIVE AND ANTI-CANCER COMPOSITION COMPRISING SAME AS ACTIVE INGREDIENT

CROSS-REFERENCE TO RELATED APPLICATION

This application is the U.S. national phase applications filed under 35 U.S.C.§371 claims benefit to International Patent Application No. PCT/KR2012/008989, filed on Oct. 30, 2012, which is entitled to priority under 35 U.S.C §119(a)-(d) to Korea application no. 10-2012-0016246, filed on Feb. 17, 2012, the disclosure of which is incorporated herein by reference in its entirety.

BACKGROUND

1. Field of the Invention

The present invention relates to a novel 2-aminothiazole derivative, N-(5-(4-fluorophenyl)thiazol-2-yl)-3-(furan-2-yl)propanamide, and an anti-cancer composition including the same as an active ingredient.

2. Discussion of Related Art

Cancer, also known as a malignant neoplasm, is a disease in which a group of cells cause uncontrolled growth, invasion, and sometimes metastasis, and leads major world health problems. Cancer is a disease which results in uncontrolled growth of cells due to failure of frequency control of cell cycles. Further, cancer is considered a disease which results in uncontrolled growth of cells, in which survival signals are continuously provided in order to inhibit apoptosis. Therefore, frequency control of cell cycles and control of apoptosis are considered effective methods of treating cancer (Blank, M.; Shiloh: Programs for cell death. Cell Cycle 6: 686-695, 2007). However, it takes several years to develop a drug for treating cancer and substantially provide benefits of the drug to patients. The duration is a very long period of time, and should be lowered for patients to rapidly obtain benefits from new technologies and development ideas for drugs.

Combinatorial chemistry is widely used as a technique and a tool from biology and chemistry fields in order to accelerate discovery and development of new drugs [1,2]. Thiazole derivatives are present in many natural and synthetic products, and have various pharmacological activities such as an anti-cancer activity, an antiviral activity, an antibiotic activity, an antifungal activity and an anti-inflammatory activity (Conrath, U.; Pieterse, C. M.; Mauch-Mani, B. Trends. Plant Sci. 2002, 7, 210). Among them, 2-aminothiazole derivatives are known to have an anti-cancer activity obtained through kinase inhibition [3-5].

A number of papers and patent documents have been cited throughout the present specification. The content of the cited papers and patent documents is incorporated herein by reference and the level of technical field of the present invention and the contents of the present invention will be described more clearly.

SUMMARY OF THE INVENTION

As a result of research for the development of a candidate anti-cancer compound, the present inventors found that a synthesized novel 2-aminothiazole derivative compound has a specific cytotoxicity activity against cancer cells and in-vivo anti-cancer efficacy which inhibits growth of a tumor in an animal in which cancer cells are transplanted, and therefore achieved the present invention.

Therefore, the present invention is directed to a novel 2-aminothiazole derivative.

The present invention is directed to an anti-cancer composition including a novel 2-aminothiazole derivative as an active ingredient.

The present invention is directed to a method of treating or preventing cancer including administrating an anti-cancer pharmaceutical composition including a novel 2-aminothiazole derivative as an active ingredient to a subject requiring cancer treatment.

The present invention is directed to a pharmaceutical composition including a novel 2-aminothiazole derivative for use in a method of treating cancer.

The present invention is directed to use of a novel 2-aminothiazole derivative for the preparation of a composition for treating or preventing cancer.

Objects and advantages of the present invention will be described more clearly by the following detailed description of the present invention, claims, and drawings.

According to an aspect of the present invention, there is provided a 2-aminothiazole derivative represented by Chemical Formula 1 or a pharmaceutically acceptable salt thereof.

[Chemical Formula 1]

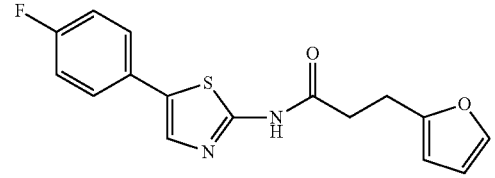

According to another aspect of the present invention, there is provided an anti-cancer pharmaceutical composition including, as an active ingredient, a 2-aminothiazole derivative represented by Chemical Formula 1 or a pharmaceutically acceptable salt thereof.

The active component of the composition according to the present invention is a 2-aminothiazole derivative, N-(5-(4-fluorophenyl)thiazol-2-yl)-3-(furan-2-yl)propanamide represented by Chemical Formula 1.

Thiazole derivatives are present in many natural and synthetic products, and have various physiological activities such as an anti-cancer activity, an antiviral activity, an antimicrobial activity, an antifungal activity and an anti-inflammatory activity.

The term "pharmaceutically acceptable salt" in the specification generally refers to an acid-addition salt or a base-addition salt which is formed of a suitable non-toxic organic acid or inorganic acid, or non-toxic organic base or inorganic base and has biological efficacy and properties of the compound according to the present invention. Examples of the acid-addition salt include an acid-addition salt derived from an inorganic acid such as hydrochloric acid, hydrobromic acid, hydroiodic acid, sulfuric acid, sulfamic acid, phosphoric acid, and nitric acid, or an acid-addition salt derived from an organic acid such as p-toluenesulfonic acid, salicylic acid, methanesulfonic acid, oxalic acid, succinic acid, citric acid, malic acid, lactic acid, or fumaric acid. Examples of the base-addition salt include a base-addition salt derived from ammonium, potassium, sodium, and a quaternary ammonium hydroxide such as tetramethylammonium hydroxide. In order to obtain improved physical and chemical stability, hygroscopic property, fluidity, and solubility of the compound, a pharmaceutical compound (i.e., drug) is chemically converted into a salt, which is widely known in pharmaceutical chemistry (H. Ansel et al., Pharmaceutical Dosage Forms and Drug Delivery Systems (6th Ed. 1995) at pp. 196 and 1456-1457).

The term "pharmaceutically acceptable" in the specification means that for example, a pharmaceutically acceptable carrier, excipient, or the like may be pharmaceutically tolerable and substantially non-toxic to a patient to which a specific compound is administrated.

The compound according to the present invention has a cytotoxicity activity against various cancer cells and an activity which inhibits growth of a tumor in an animal model in which cancer cells are transplanted, as proved in the following specific example. Therefore, the compound according to the present invention has a very superior anti-cancer activity.

Examples of the cancer capable of being treated or prevented by the compound according to the present invention include breast cancer, lung cancer, stomach cancer, liver cancer, blood cancer, bone cancer, pancreatic cancer, skin cancer, head or neck cancer, skin or eye melanoma, sarcoma of the uterus, ovarian cancer, rectal cancer, anal cancer, colorectal cancer, fallopian tube carcinoma, endometrium carcinoma, cervical cancer, small intestine cancer, endocrine gland cancer, thyroid cancer, parathyroid gland cancer, renal cell carcinoma, soft tissue sarcoma, urethra cancer, prostate cancer, bronchial cancer, myeloma, neuroma, cutaneous squamous cell carcinoma, or the like, but are not limited thereto. Among them, lung cancer, skin cancer, colorectal cancer, prostate cancer, ovarian cancer, or breast cancer is preferable.

The pharmaceutical composition according to the present invention includes, as an active ingredient, a pharmaceutically acceptable carrier as well as a 2-aminothiazole derivative or a pharmaceutically acceptable salt thereof.

The pharmaceutically acceptable carrier is generally used at the time of formulation, and examples thereof include lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate, mineral oil, or the like, but are not limited thereto.

In addition to the above, the pharmaceutical composition according to the present invention may further include a lubricant, a wetting agent, a sweetener, a fragrance, an emulsifier, a suspending agent, a preservative, or the like. Suitable pharmaceutically acceptable carriers and formulation thereof are described in detail in Remington's Pharmaceutical Sciences (19th ed., 1995).

Adequate dose of the pharmaceutical composition according to the present invention may be determined according to various factors, including methods of formulation, administration modes, ages, weights, sex, pathological conditions and diet of patients, administration periods, administration routes, excretion rates and reaction sensitivity. Meanwhile, oral dosage of the pharmaceutical composition according to the present invention may be 0.01-1000 mg/kg weight per day.

The pharmaceutical composition according to the present invention may be administered orally or parenterally. Examples of the parenteral administration may include local application on the skin, intravenous injection, subcutaneous injection, muscular injection, intraperitoneal injection, transdermal administration, or the like.

Density of the active ingredient, the 2-aminothiazole derivative, in the composition according to the present invention may be determined in view of therapeutic purposes, a patient's conditions, duration, or the like, but is not limited to a specific range.

The pharmaceutical composition according to the present invention may be formulated using a pharmaceutically acceptable carrier and/or an excipient by those skilled in the art and prepared in a unit dose form or be contained in a multi-dose container. In this case, the formulation may be a solution in oil or an aqueous medium, a suspension or emulsion, an extract, a powder, granules, a tablet, or a capsule, and may further include a dispersing or stabilizing agent.

According to still another aspect of the present invention, there is provided a method of treating or preventing cancer including administrating an anti-cancer pharmaceutical composition including, as an active ingredient, a 2-aminothiazole derivative represented by Chemical Formula 1 or a pharmaceutically acceptable salt thereof to a subject requiring cancer treatment.

According to one embodiment of the present invention, the cancer may be lung cancer, skin cancer, colorectal cancer, prostate cancer, ovarian cancer, or breast cancer.

According to yet another aspect of the present invention, there is provided a pharmaceutical composition including a 2-aminothiazole derivative represented by Chemical Formula 1 or a pharmaceutically acceptable salt thereof for use in a method of treating cancer.

According to one embodiment of the present invention, the cancer may be lung cancer, skin cancer, colorectal cancer, prostate cancer, ovarian cancer, or breast cancer.

According to yet another aspect of the present invention, there is provided use of a 2-aminothiazole derivative represented by Chemical Formula 1 or a pharmaceutically acceptable salt thereof for the preparation of a composition for treating or preventing cancer.

According to one embodiment of the present invention, the cancer may be lung cancer, skin cancer, colorectal cancer, prostate cancer, ovarian cancer, or breast cancer.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
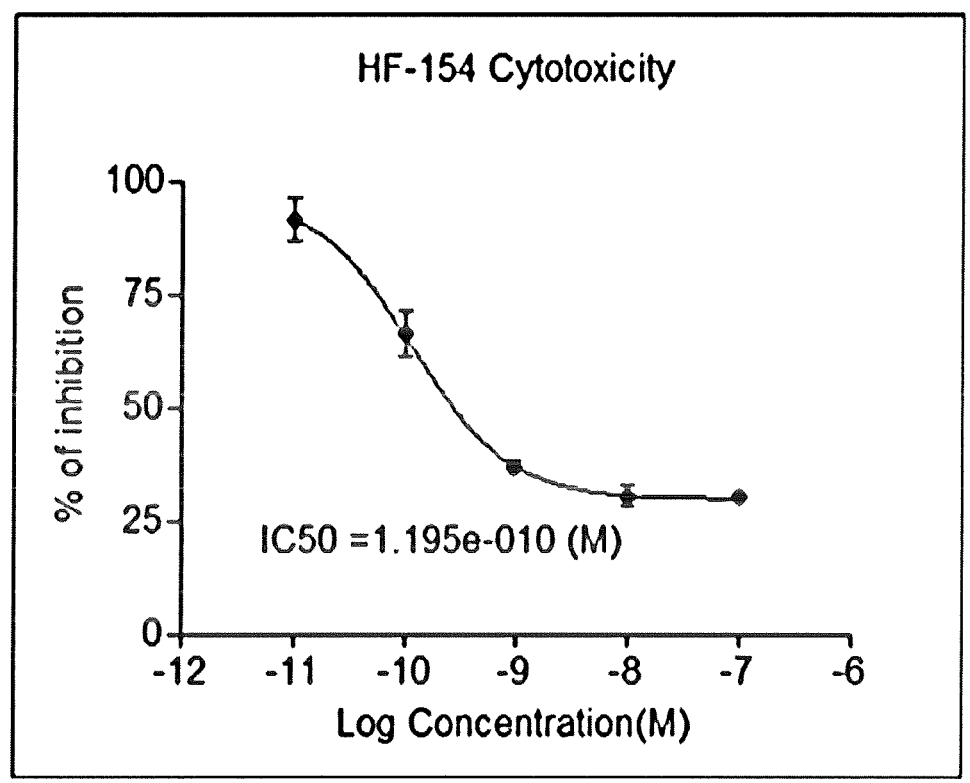
FIG. 1 is a graph showing a measurement result of cytotoxicity of the compound according to the present invention, N-(5-(4-fluorophenyl)thiazol-2-yl)-3-(furan-2-yl) propanamide (HF-154), against a prostate cancer cell line, PC3.

Hereinafter, the present invention will be described in detail with reference to Examples. It is clear to those skilled in the art that Examples are intended to specifically describe the present invention, and do not limit the scope of the present invention according to the gist of the present invention.

EXAMPLES

Example 1

Synthesis of N-(5-bromo-2-thiazolyl)-2-furanpropanamide

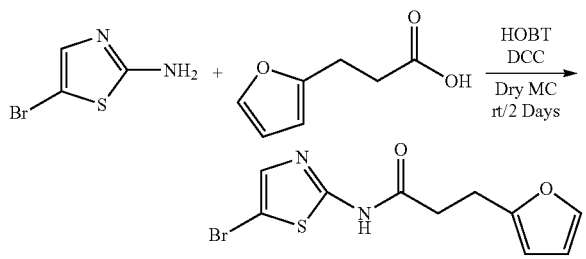

3-(2-furyl)propionic acid (3.85 mmoles), N,N'-dicyclohexyl carbodiimide (3.85 mmoles), and hydroxybenzotriazole (0.385 mmoles) were dissolved in dry methylene chloride (MC) (40 mL), followed by stirring for 1.5 hours at room temperature under nitrogen. 2-amino-5-bromothiazole monohydrobromide (3.85 mmoles) was added thereto, and then the reaction mixture was stirred for two days at room temperature. Reaction completion was checked by thin layer chromatography (TLC). After reaction completion, the reaction mixture was quenched with water. The reaction mixture was separated using MC and distilled water. The separated organic layer was dehydrated using anhydrous MgSO$_4$. The reaction mixture was concentrated under reduced pressure to remove a solvent, dissolved in a small amount of MC, and then separated by flash column chromatography. Finally, 0.772 g (66.67%) of N-(5-bromo-2-thiazolyl)-2-furanpropanamide was produced as light yellow crystals.

$^1$H NMR(300 MHz, CDCl$_3$) δ10.53(s, 1H), 7.34-7.32(d, 2H), 6.28(t, 1H), 6.08(d, 1H), 3.11(m, 2H), 2.82(m, 2H).

Example 2

Synthesis of N-(5-(4-fluorophenyl)thiazol-2-yl)-3-(furan-2-yl)propanamide

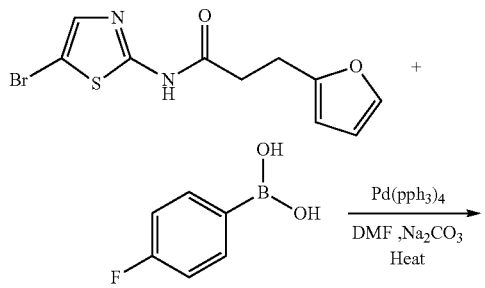

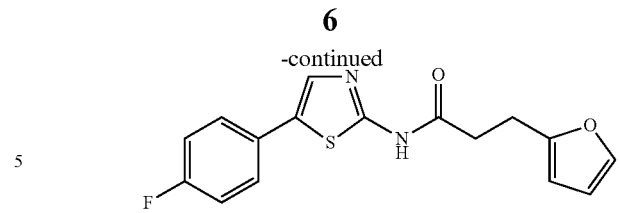

N-(5-bromo-2-thiazolyl)-2-propanamide (600 mg, 1.99 mmoles), 4-fluorophenyl boric acid (0.42 g, 2.99 mmoles), and sodium carbonate anhydride (1.05 g, 9.95 mmoles) were dissolved in dimethyl fluoride (DMF, 18 mL) and H$_2$O (0.6 mL), followed by stirring for 1.5 hours at room temperature. After stirring, the reaction mixture was maintained for 5 minutes under nitrogen. Tetrakis(triphenylphosphine)-palladium (0.68 g, 0.588 mmoles) was added thereto, and then maintained at 80° C. in an oil bath, followed by stirring overnight. Reaction completion was checked by TLC. After reaction completion, the reaction mixture was quenched with distilled water. The reaction mixture was separated using MC and distilled water. The separated organic layer was dehydrated using anhydrous MgSO$_4$. The reaction mixture was concentrated under reduced pressure to remove a solvent, dissolved in a small amount of MC, and then separated by flash column chromatography. The purified product was recrystallized by hexane and ethylacetate (HEX-EA) to obtain 16.8 mg (2.7%) of a white crystalline compound.

The synthesized compound, N-(5-(4-fluorophenyl)thiazol-2-yl)-3-(furan-2-yl)propanamide was named HF-154, and used for the measurement of the anti-cancer activity in the following Examples.

$^1$H NMR (300 MHz, CDCl$_3$) δ10.68(s, 1H), 7.52(m, 2H), 7.31(d, 1H), 7.09(t, 2H), 6.29(t, 1H), 6.10(d, 1H), 3.14(t, 2H), 2.87(t, 2H).

Example 3

Cytotoxicity Activity Against Cancer Cells (1) Cell Culture

The prostate cancer cell line, PC3 was obtained from Korean Cell Line Bank. After adding Rosewell Park Memorial Institute (RPMI) 1640 cell culture medium (LM001-01, WelGEN) containing 10% fetal bovine serum (FBS), 100 units/mL of penicillin and 100 μg/mL of streptomycin to a 100 Φ dish, cells were inoculated on the dish and cultured in a CO$_2$ incubator (VS-9000C, vision) in 5% CO$_2$/95% humidified air atmosphere at 37° C. When the dish was filled with cells by 80%, the cells were observed with a microscope and subcultured using phosphate buffered saline (PBS) and a 0.05% trypsin-ethylene diamine tetraacetic acid (EDTA) solution.

(2) Measurement of Cytotoxicity Activity Against Cancer Cells through MTT Analysis Toxicity to cells was analyzed using 3-[4,5-dimethylthiazol-2-yl]-2,5-diphenyl-tetra zolium bromide (MTT) analysis. As cancer cells to be measured, 8.0×10$^3$ cells/mL was aliquoted on a 96-well culture dish and then the cells were cultured for 24 hours. The next day, the synthesized compound was dissolved in a medium according to each concentration, and diluted in a medium according to each concentration. The medium in which the compound was dissolved according to each concentration was added to a culture dish at 1 mL, dimethyl sulfoxide (DMSO) was added to a control well so as to have the same volume as the added compound. After the addition, the cells were cultured in an incubator in 5% $CO_2$ at 37° C., and then survival capability of cells was measured at 24 hours and 48 hours after the culture. After the medium was removed, the cells were washed twice using PBS, then 200 μL of a solution containing 1 mg/mL of MTT (Sigma-Aldrich Chemical Co., USA) was added thereto, and then the cells were further cultured for 3 hours in a $CO_2$ incubator at 37° C. The 96-well culture dish was centrifuged for 10 minutes at 2000 rpm to remove the MTT solution. DMSO was added to each well at 200 μL and shaken for 15 minutes to dissolve the produced purple crystals. The solution was added to the 96-well culture dish, and then absorbance was measured at 540 nm. Relative absorbance was calculated using absorbance according to concentration of drugs divided by absorbance of a control group (drug-untreated group).

As an experiment result by MTT analysis, it could be found that the compound according to the present invention, HF-154 has an $IC_{50}$ value of about 0.1 nM in a prostate cancer cell line, PC3, and a very superior anti-cancer activity for prostate cancer (see FIG. 1 and Table 1). Further, a cytotoxicity effect of the compound, HF-154, was measured against each of lung cancer cells (A549), skin cancer cells (SK-MEL2), colorectal cancer cells (HCT15), ovarian cancer cells (SK-OV-3) and breast cancer cells (MCF7), and a result is shown in Table 1. In addition to the prostate cancer cells, it was found that ovarian cancer cells (SK-OV-3) and breast cancer cells (MCR7) have $IC_{50}$ values of about 0.5 nM and 0.3 nM, respectively, lung cancer cells (A549), skin cancer cells (SK-MEL2), colorectal cancer cells (HCT15) each have an $IC_{50}$ value of about 1 to 5 nM, and therefore the compound has superior anti-cancer efficacy to other cancer cells as well as prostate cancer cells.

TABLE 1

| | $IC_{50}$ (nM) | | | | | |
|---|---|---|---|---|---|---|
| Cancer cell | A549 Lung cancer | SK-OV3 Ovarian cancer | SK-MEL2 Skin cancer | HCT15 Colorectal cancer | PC3 Prostate cancer | MCF7 Breast cancer |
| HF154 | ~3 | 0.5 | ~5 | ~1 | ~0.1 | ~0.3 |

Example 4

Measurement of Anti-Cancer Effect in In-Vivo using Mice with Tumors

Figure 2:
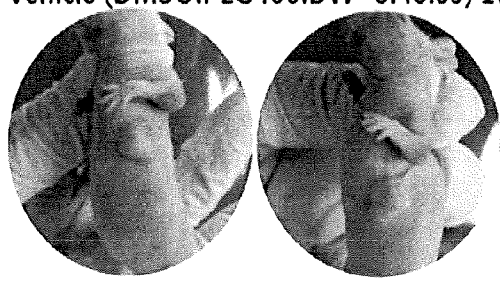
FIG. 2 is a photograph showing a result of inhibiting growth of a tumor by the compound according to the present invention, N-(5-(4-fluorophenyl)thiazol-2-yl)-3-(furan-2-yl) propanamide (HF-154), in mice in which a prostate cancer cell line, PC3, is transplanted.
Figure 2:
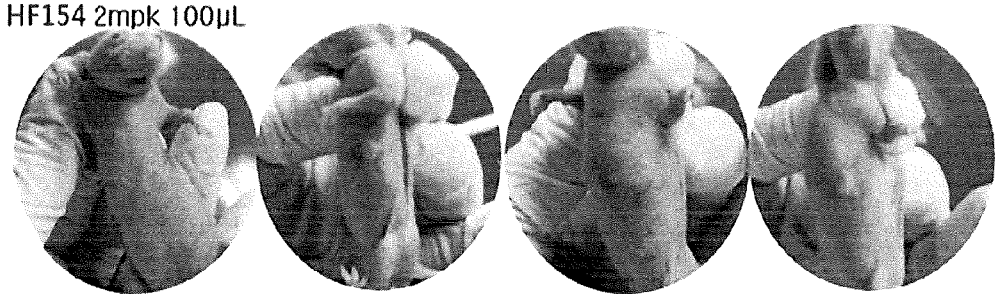
Figure 3:
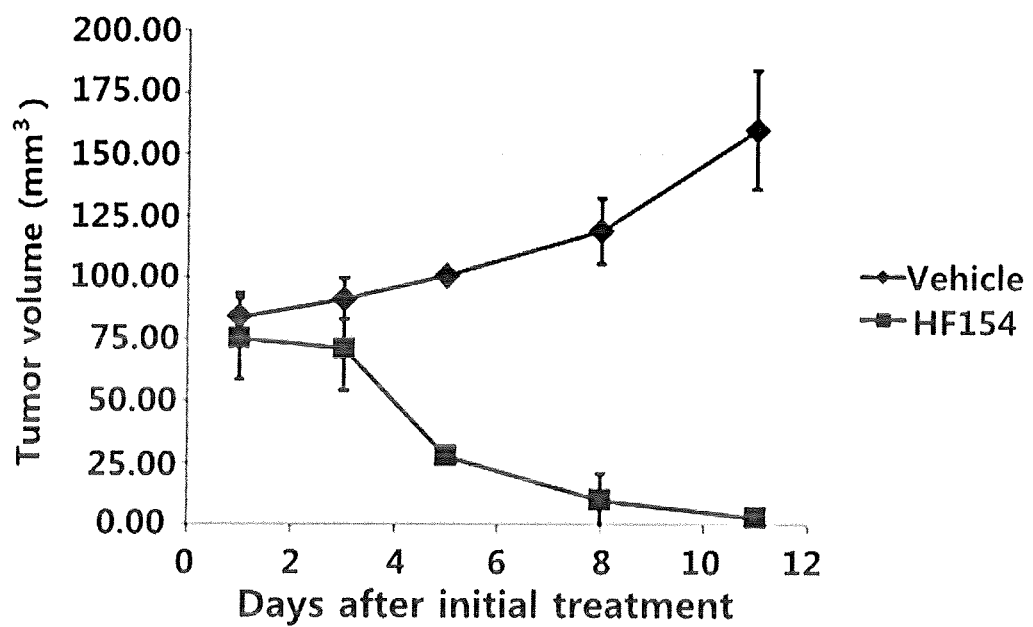
FIG. 3 is a graph showing a result of inhibiting growth of a tumor by the compound according to the present invention, N-(5-(4-fluorophenyl)thiazol-2-yl)-3-(furan-2-yl)propanamide (HF-154), in mice in which a prostate cancer cell line, PC3, is transplanted.

The anti-cancer activity of the compound according to the present invention, HF-154 was measured in in-vivo using mice in which a prostate cancer cell line, PC3, was transplanted. An experimental group included a group of two mice to which an excipient (vehicle) was administered and a group of four mice to which the compound according to the present invention, HF-154, was administered. The compound according to the present invention, HF-154, was administered to each mouse in an amount of 2 mg/kg/day (100 μL i.v.). First, after administration for four consecutive days, administration was stopped, and tumor growth was compared at 7 days after the stoppage. As shown in FIGS. 2 and 3, it could be found that the size of the tumor of cancer cells transplanted to the mice to which the compound according to the present invention, HF-154, was administered was significantly reduced, compared to the excipient administration group.

The present invention relates to a novel 2-aminothiazole derivative, N-(5-(4-fluorophenyl)thiazol-2-yl)-3-(furan-2-yl)propanamide, and use thereof as an anti-cancer drug. The compound according to the present invention is found to have a very superior specific cytotoxicity activity against cancer cells and an in-vivo anti-cancer activity which inhibits growth of a tumor in an animal model in which cancer cells are transplanted, and hence may be developed as a candidate anti-cancer compound.

It is clear to those skilled in the art that the specific portion of the present invention was described in detail above, in which the specific technique is only one embodiment and does not limit the scope of the present. Therefore, the substantial scope of the present invention will be defined by the appended claims and their equivalents.

REFERENCES

1. Hook A L, et al. Biomaterials 2: 187-198, 2010.
2. Foley P L and Shuler M L: Biotechnol Bioeng 105: 26-36, 2010.
3. Kim, K. S. et al. J. Med. Chem. 2002, 45, 3905.
4. Misra, R. N. et al. J. Med. Chem. 2004, 47, 1719.
5. Borzilleri, R. M. et al. J. Med. Chem. 2006, 49, 3766.
6. Kim K S, Kimball S D, Misra R N, et al.: J Med Chem 45: 3905-3927, 2002.
7. Misra R N, Xiao H Y, Kim K S, et al.: J Med Chem 47: 1719-1728, 2004.
8. Jung F H, Pasquet G, Lambert-van der Brempt C, et al.: J Med Chem 49: 955-970, 2006.
9. Borzilleri R M, Bhide R S, Banish J C, et al.: J Med Chem 49: 1 3766-3769, 2006.
10. Kuramoto M, Sakata Y, Terai K, et al.: Org Biomol Chem 6: 2772-2781, 2008.
11. Romagnoli R, Baraldi P G, Carrion M D, et al.: J Med Chem 52: 5551-5555, 2009.
12. Christopher J. Helal, Mark A. et al.: Bioorg Med Chem Lett 14: 5521-5525, 2004.

What is claimed is:

1. A method of reducing the size of a tumor associated with prostate cancer in a subject, comprising administering an anti-cancer pharmaceutical composition including, as an active ingredient, a 2-aminothiazole derivative represented by Chemical Formula 1 or a pharmaceutically acceptable salt thereof to a subject requiring cancer treatment:

[Chemical Formula 1]

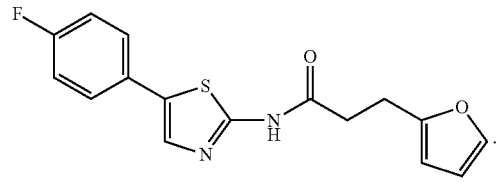

* * * * *